United States Patent
Hoffman (10) Patent No.: US 9,901,434 B2
(45) Date of Patent: Feb. 27, 2018

(54) EMBOLIC PROTECTION DEVICE INCLUDING A Z-STENT WAIST BAND

(75) Inventor: Grant T. Hoffman, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 1850 days.

(21) Appl. No.: 12/038,238

(22) Filed: Feb. 27, 2008

(65) Prior Publication Data

US 2008/0208245 A1 Aug. 28, 2008

Related U.S. Application Data

(60) Provisional application No. 60/903,791, filed on Feb. 27, 2007.

(51) Int. Cl.
*A61M 29/00* (2006.01)
*A61F 2/01* (2006.01)

(52) U.S. Cl.
CPC .......... *A61F 2/01* (2013.01); *A61F 2002/018* (2013.01); *A61F 2230/0006* (2013.01); *A61F 2230/008* (2013.01)

(58) Field of Classification Search
CPC .............................. A61F 2002/018; A61F 2/01
USPC ....... 606/110, 113, 127, 159, 108, 198, 200, 606/213, 215; 623/1.11, 1.12, 901–903; 604/104–107; 128/830, 831, 833, 840, 128/843
See application file for complete search history.

(56) References Cited

U.S. PATENT DOCUMENTS

| | | |
|---|---|---|
| 3,108,593 A | 10/1963 | Glassman |
| 3,334,629 A | 8/1967 | Cohn |
| 3,472,230 A | 10/1969 | Fogarty |
| 3,547,103 A | 12/1970 | Cook |
| 3,635,223 A | 1/1972 | Klieman |

(Continued)

FOREIGN PATENT DOCUMENTS

| | | |
|---|---|---|
| DE | 3429850 A1 | 2/1986 |
| EP | 1127556 A2 | 8/2001 |

(Continued)

OTHER PUBLICATIONS

Dictionary.com definition of "about"; http://dictionary.reference.com/browse/about.*

(Continued)

*Primary Examiner* — Gregory Anderson
*Assistant Examiner* — Sarah Simpson
(74) *Attorney, Agent, or Firm* — Brinks Gilson & Lione (57) ABSTRACT

An embolic protection device for capturing emboli in a body vessel having a frame and a z-stent waist band. The frame includes a plurality of struts configured to open radially to define an expanded state of the device for capturing emboli and to fold along the longitudinal axis to define a collapsed state of the device for deployment and retrieval. The waist band has an open and a closed state and is attached to within the frame between a proximal and distal end. The waist band is formed of a plurality of members attached at a joint to an adjacent member such that the members lie substantially parallel in the closed state and form a "Z" pattern in the open state. A filter portion is attached to the waist band and configured to capture emboli in the expanded state.

25 Claims, 4 Drawing Sheets (56) References Cited

U.S. PATENT DOCUMENTS

| | | | |
|---|---|---|---|
| 3,923,065 A | 12/1975 | Nozick et al. |
| 3,952,747 A | 4/1976 | Kimmell, Jr. |
| 3,978,863 A | 9/1976 | Fettel et al. |
| 3,996,938 A | 12/1976 | Clark, III |
| 4,425,908 A | 1/1984 | Simon |
| 4,456,000 A | 6/1984 | Schjeldahl et al. |
| 4,494,531 A | 1/1985 | Gianturco |
| 4,548,206 A | 10/1985 | Osborne |
| 4,561,439 A | 12/1985 | Bishop et al. |
| 4,562,039 A | 12/1985 | Koehler |
| 4,604,094 A | 8/1986 | Shook |
| 4,619,246 A | 10/1986 | Molgaard-Nielsen et al. |
| 4,643,184 A | 2/1987 | Mobin-Uddin |
| 4,646,736 A | 3/1987 | Auth |
| 4,650,472 A | 3/1987 | Bates |
| 4,665,906 A | 5/1987 | Jervis |
| 4,669,464 A | 6/1987 | Sulepov |
| 4,688,553 A | 8/1987 | Metals |
| 4,723,549 A | 2/1988 | Wholey et al. |
| 4,727,873 A | 3/1988 | Mobin-Uddin |
| 4,732,152 A | 3/1988 | Wallsten et al. |
| 4,817,600 A | 4/1989 | Herms et al. |
| 4,824,435 A | 4/1989 | Giesy et al. |
| 4,832,055 A | 5/1989 | Palestrant |
| 4,846,794 A | 7/1989 | Hertzer |
| 4,848,343 A | 7/1989 | Wallsten et al. |
| 4,873,978 A | 10/1989 | Ginsburg |
| 4,943,297 A | 7/1990 | Saveliev et al. |
| 4,957,501 A | 9/1990 | Lahille et al. |
| 4,990,156 A | 2/1991 | Lefebvre |
| 4,998,916 A | 3/1991 | Hammerslag et al. |
| 5,053,008 A | 10/1991 | Bajaj |
| 5,059,205 A | 10/1991 | El-Nounou et al. |
| 5,069,226 A | 12/1991 | Yamauchi et al. |
| 5,078,726 A | 1/1992 | Kreamer |
| 5,100,423 A | 3/1992 | Fearnot |
| 5,108,418 A | 4/1992 | Lefebvre |
| 5,108,419 A | 4/1992 | Reger et al. |
| 5,112,347 A | 5/1992 | Taheri |
| 5,129,890 A | 7/1992 | Bates et al. |
| 5,133,733 A | 7/1992 | Rasmussen et al. |
| 5,147,379 A | 9/1992 | Sabbaghian et al. |
| 5,152,777 A | 10/1992 | Goldberg |
| 5,160,342 A | 11/1992 | Reger |
| 5,163,927 A | 11/1992 | Woker et al. |
| 5,203,772 A | 4/1993 | Hammerslag et al. |
| 5,234,458 A | 8/1993 | Metais |
| 5,242,462 A | 9/1993 | El-Nounou |
| 5,243,996 A | 9/1993 | Hall |
| 5,251,640 A | 10/1993 | Osborne |
| 5,263,964 A | 11/1993 | Purdy |
| 5,300,086 A | 4/1994 | Gory et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,397 A | 9/1994 | Palermo et al. |
| 5,350,398 A | 9/1994 | Pavcnik et al. |
| 5,364,345 A | 11/1994 | Lowery et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,417,708 A | 5/1995 | Hall et al. |
| 5,451,233 A | 9/1995 | Yock |
| 5,458,573 A | 10/1995 | Summers |
| 5,522,881 A | 6/1996 | Lentz |
| 5,527,338 A | 6/1996 | Purdy |
| 5,531,788 A | 7/1996 | Dibie et al. |
| 5,549,551 A | 8/1996 | Peacock et al. |
| 5,549,626 A | 8/1996 | Miller et al. |
| 5,556,414 A | 9/1996 | Turi |
| 5,562,698 A | 10/1996 | Parker |
| 5,571,135 A | 11/1996 | Fraser et al. |
| 5,591,195 A | 1/1997 | Taheri et al. |
| 5,601,595 A | 2/1997 | Smith |
| 5,624,461 A | 4/1997 | Mariant |
| 5,626,605 A | 5/1997 | Irie et al. |
| 5,630,797 A | 5/1997 | Diedrich et al. |
| 5,634,942 A | 6/1997 | Chevillon et al. |
| 5,649,953 A | 7/1997 | Lefebvre |
| 5,662,703 A | 9/1997 | Yurek et al. |
| 5,669,933 A | 9/1997 | Simon et al. |
| 5,681,347 A | 10/1997 | Cathcart et al. |
| 5,690,642 A | 11/1997 | Osborne et al. |
| 5,690,667 A | 11/1997 | Gia |
| 5,693,067 A | 12/1997 | Purdy |
| 5,693,087 A | 12/1997 | Parodi |
| 5,695,518 A | 12/1997 | Laerum |
| 5,695,519 A | 12/1997 | Summers et al. |
| 5,700,253 A | 12/1997 | Parker |
| 5,709,704 A | 1/1998 | Nott et al. |
| 5,713,853 A | 2/1998 | Clark et al. |
| 5,720,764 A | 2/1998 | Naderlinger |
| 5,725,550 A | 3/1998 | Nadal |
| 5,738,667 A | 4/1998 | Solar |
| 5,746,767 A | 5/1998 | Smith |
| 5,755,772 A | 5/1998 | Evans et al. |
| 5,755,790 A | 5/1998 | Chevillon et al. |
| 5,766,203 A | 6/1998 | Imran et al. |
| 5,769,816 A * | 6/1998 | Barbut et al. ............. 604/93.01 |
| 5,769,871 A | 6/1998 | Mers et al. |
| 5,795,322 A | 8/1998 | Boudewijn |
| 5,800,457 A | 9/1998 | Gelbfish et al. |
| 5,800,525 A | 9/1998 | Bachinski et al. |
| 5,810,874 A | 9/1998 | Lefebvre |
| 5,814,027 A | 9/1998 | Hassett et al. |
| 5,814,064 A | 9/1998 | Daniel et al. |
| 5,820,592 A | 10/1998 | Hammerslag |
| 5,827,324 A | 10/1998 | Cassell et al. |
| 5,830,230 A | 11/1998 | Berryman et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,876,367 A | 3/1999 | Kaganov et al. |
| 5,893,869 A | 4/1999 | Barnhart et al. |
| 5,895,391 A | 4/1999 | Farnholtz |
| 5,895,399 A | 4/1999 | Barbut et al. |
| 5,895,410 A | 4/1999 | Forber et al. |
| 5,908,435 A | 6/1999 | Samuels |
| 5,910,154 A | 6/1999 | Tsugita et al. |
| 5,911,702 A | 6/1999 | Romley et al. |
| 5,911,704 A | 6/1999 | Humes |
| 5,911,717 A | 6/1999 | Jacobsen et al. |
| 5,911,734 A | 6/1999 | Tsugita et al. |
| 5,919,224 A | 7/1999 | Thompson et al. |
| 5,925,062 A | 7/1999 | Purdy |
| 5,925,063 A | 7/1999 | Khosravi |
| 5,928,260 A | 7/1999 | Chine et al. |
| 5,928,261 A | 7/1999 | Ruiz |
| 5,938,683 A | 8/1999 | Lefebvre |
| 5,941,896 A | 8/1999 | Kerr |
| 5,944,728 A | 8/1999 | Bates |
| 5,947,985 A | 9/1999 | Imran |
| 5,947,995 A | 9/1999 | Samuels |
| 5,948,017 A | 9/1999 | Taheri |
| 5,951,567 A | 9/1999 | Javier, Jr. et al. |
| 5,954,741 A | 9/1999 | Fox |
| 5,954,742 A | 9/1999 | Osypka |
| 5,954,745 A | 9/1999 | Gertler et al. |
| 5,968,057 A | 10/1999 | Taheri |
| 5,968,071 A | 10/1999 | Chevillon et al. |
| 5,972,019 A | 10/1999 | Engelson et al. |
| 5,976,162 A | 11/1999 | Doan et al. |
| 5,976,172 A | 11/1999 | Homsma et al. |
| 5,980,555 A | 11/1999 | Barbut et al. |
| 5,984,947 A | 11/1999 | Smith |
| 5,984,965 A | 11/1999 | Knapp et al. |
| 5,989,281 A | 11/1999 | Barbut et al. |
| 6,001,118 A | 12/1999 | Daniel et al. |
| 6,007,557 A | 12/1999 | Ambrisco et al. |
| 6,007,558 A * | 12/1999 | Ravenscroft et al. ........ 606/200 |
| 6,010,522 A | 1/2000 | Barbut et al. |

(56) References Cited

U.S. PATENT DOCUMENTS

| | | | |
|---|---|---|---|
| 6,013,093 A | 1/2000 | Nott et al. | |
| 6,015,424 A | 1/2000 | Rosenbluth et al. | |
| 6,027,520 A | 2/2000 | Tsugita et al. | |
| 6,036,717 A | 3/2000 | Mers Kelly et al. | |
| 6,036,720 A | 3/2000 | Abrams et al. | |
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,745 A | 5/2000 | Gelbfish | |
| 6,059,813 A | 5/2000 | Vrba et al. | |
| 6,059,814 A | 5/2000 | Ladd | |
| 6,063,113 A | 5/2000 | Kavteladze et al. | |
| 6,066,158 A | 5/2000 | Engelson et al. | |
| 6,068,645 A | 5/2000 | Tu | |
| 6,074,357 A | 6/2000 | Kaganov et al. | |
| 6,077,274 A | 6/2000 | Ouchi et al. | |
| 6,080,178 A | 6/2000 | Meglin | |
| 6,083,239 A | 7/2000 | Addis | |
| 6,086,577 A | 7/2000 | Ken et al. | |
| 6,086,605 A | 7/2000 | Barbut et al. | |
| 6,093,199 A | 7/2000 | Brown et al. | |
| 6,096,053 A | 8/2000 | Bates | |
| 6,096,070 A | 8/2000 | Ragheb et al. | |
| 6,099,549 A | 8/2000 | Bosma et al. | |
| 6,106,497 A | 8/2000 | Wang | |
| 6,126,672 A | 10/2000 | Berryman et al. | |
| 6,126,673 A | 10/2000 | Kim et al. | |
| 6,129,739 A | 10/2000 | Khosravi | |
| 6,136,016 A | 10/2000 | Barbut et al. | |
| 6,146,396 A | 11/2000 | Konya et al. | |
| 6,146,404 A | 11/2000 | Kim et al. | |
| 6,152,931 A | 11/2000 | Nadal et al. | |
| 6,152,946 A | 11/2000 | Broome et al. | |
| 6,152,947 A | 11/2000 | Ambrisco et al. | |
| 6,156,061 A | 12/2000 | Wallace et al. | |
| 6,156,062 A | 12/2000 | McGuinness | |
| 6,159,230 A | 12/2000 | Samuels | |
| 6,165,179 A | 12/2000 | Cathcart et al. | |
| 6,165,198 A | 12/2000 | McGurk et al. | |
| 6,165,199 A | 12/2000 | Barbut | |
| 6,165,200 A * | 12/2000 | Tsugita et al. | 606/200 |
| 6,168,579 B1 | 1/2001 | Tsugita et al. | |
| 6,168,603 B1 | 1/2001 | Leslie et al. | |
| 6,168,610 B1 | 1/2001 | Marin et al. | |
| 6,168,622 B1 | 1/2001 | Mazzocchi | |
| 6,171,327 B1 | 1/2001 | Daniel et al. | |
| 6,171,328 B1 | 1/2001 | Addis | |
| 6,174,318 B1 | 1/2001 | Bates et al. | |
| 6,179,851 B1 | 1/2001 | Barbut et al. | |
| 6,179,859 B1 | 1/2001 | Bates et al. | |
| 6,179,860 B1 | 1/2001 | Fulton, III et al. | |
| 6,179,861 B1 | 1/2001 | Khosravi et al. | |
| 6,187,025 B1 | 2/2001 | Machek | |
| 6,193,739 B1 | 2/2001 | Chevillon et al. | |
| 6,203,561 B1 | 3/2001 | Ramee et al. | |
| 6,206,931 B1 | 3/2001 | Cook et al. | |
| 6,214,025 B1 | 4/2001 | Thistle et al. | |
| 6,214,026 B1 | 4/2001 | Lepak et al. | |
| 6,221,091 B1 | 4/2001 | Khosravi | |
| 6,224,620 B1 | 5/2001 | Maahs | |
| 6,231,588 B1 | 5/2001 | Zadno-Azizi | |
| 6,231,589 B1 | 5/2001 | Wessman et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,241,746 B1 | 6/2001 | Bosma et al. | |
| 6,245,087 B1 | 6/2001 | Addis | |
| 6,245,088 B1 | 6/2001 | Lowery | |
| 6,245,089 B1 | 6/2001 | Daniel et al. | |
| 6,251,092 B1 | 6/2001 | Qin et al. | |
| 6,251,122 B1 | 6/2001 | Tsukernik | |
| 6,254,550 B1 | 7/2001 | McNamara et al. | |
| 6,254,633 B1 | 7/2001 | Pinchuk et al. | |
| 6,258,026 B1 | 7/2001 | Ravenscroft et al. | |
| 6,258,115 B1 | 7/2001 | Dubrul | |
| 6,258,120 B1 | 7/2001 | McKenzie et al. | |
| 6,261,305 B1 | 7/2001 | Marotta et al. | |
| 6,264,672 B1 | 7/2001 | Fisher | |
| 6,267,776 B1 | 7/2001 | O'Connell | |
| 6,267,777 B1 | 7/2001 | Bosma et al. | |
| 6,273,900 B1 | 8/2001 | Nott et al. | |
| 6,273,901 B1 | 8/2001 | Whitcher et al. | |
| 6,277,125 B1 | 8/2001 | Barry et al. | |
| 6,277,126 B1 | 8/2001 | Barry et al. | |
| 6,277,138 B1 | 8/2001 | Levinson et al. | |
| 6,277,139 B1 | 8/2001 | Levinson et al. | |
| 6,280,451 B1 | 8/2001 | Bates et al. | |
| 6,287,321 B1 | 9/2001 | Jang | |
| 6,290,710 B1 | 9/2001 | Cryer et al. | |
| 6,299,604 B1 | 10/2001 | Ragheb et al. | |
| 6,306,163 B1 | 10/2001 | Fitz | |
| 6,309,399 B1 | 10/2001 | Barbut et al. | |
| 6,312,444 B1 | 11/2001 | Barbut | |
| 6,319,268 B1 | 11/2001 | Ambrisco et al. | |
| 6,325,815 B1 | 12/2001 | Kusleika et al. | |
| 6,325,816 B1 | 12/2001 | Fulton, III et al. | |
| 6,328,755 B1 | 12/2001 | Marshall | |
| 6,331,183 B1 | 12/2001 | Suon | |
| 6,331,184 B1 | 12/2001 | Abrams | |
| 6,334,864 B1 | 1/2002 | Amplatz et al. | |
| 6,336,934 B1 | 1/2002 | Gilson et al. | |
| 6,338,739 B1 | 1/2002 | Datta et al. | |
| 6,340,364 B2 | 1/2002 | Kanesaka | |
| 6,342,062 B1 | 1/2002 | Suon et al. | |
| 6,342,063 B1 | 1/2002 | DeVries et al. | |
| 6,344,048 B1 | 2/2002 | Chin et al. | |
| 6,344,049 B1 | 2/2002 | Levinson et al. | |
| 6,346,116 B1 | 2/2002 | Brooks et al. | |
| 6,348,041 B1 | 2/2002 | Klint | |
| 6,348,063 B1 | 2/2002 | Yassour et al. | |
| 6,350,721 B1 | 2/2002 | Kurz et al. | |
| 6,355,051 B1 | 3/2002 | Sisskind et al. | |
| 6,358,228 B1 | 3/2002 | Tubman et al. | |
| 6,361,545 B1 | 3/2002 | Macoviak et al. | |
| 6,361,546 B1 | 3/2002 | Khosravi | |
| 6,361,547 B1 | 3/2002 | Hieshima | |
| 6,364,895 B1 | 4/2002 | Greenhalgh | |
| 6,364,896 B1 | 4/2002 | Addis | |
| 6,368,338 B1 | 4/2002 | Konya et al. | |
| 6,371,961 B1 | 4/2002 | Osborne et al. | |
| 6,371,969 B1 | 4/2002 | Tsugita et al. | |
| 6,371,970 B1 | 4/2002 | Khosravi et al. | |
| 6,371,971 B1 * | 4/2002 | Tsugita et al. | 606/200 |
| 6,375,670 B1 | 4/2002 | Greenhalgh | |
| 6,379,374 B1 | 4/2002 | Hieshima et al. | |
| 6,380,457 B1 | 4/2002 | Yurek et al. | |
| 6,383,146 B1 | 5/2002 | Klint | |
| 6,383,171 B1 | 5/2002 | Gifford et al. | |
| 6,383,174 B1 | 5/2002 | Eder | |
| 6,383,193 B1 | 5/2002 | Cathcart et al. | |
| 6,383,196 B1 | 5/2002 | Leslie et al. | |
| 6,383,205 B1 | 5/2002 | Samson et al. | |
| 6,383,206 B1 | 5/2002 | Gillick et al. | |
| 6,391,044 B1 | 5/2002 | Yadav et al. | |
| 6,391,045 B1 | 5/2002 | Kim et al. | |
| 6,391,052 B2 | 5/2002 | Buirge et al. | |
| 6,395,014 B1 | 5/2002 | Macoviak et al. | |
| 6,402,771 B1 | 6/2002 | Palmer et al. | |
| 6,402,772 B1 | 6/2002 | Amplatz et al. | |
| 6,409,742 B1 | 6/2002 | Fulton, III et al. | |
| 6,413,235 B1 | 7/2002 | Parodi | |
| 6,416,530 B2 | 7/2002 | DeVries et al. | |
| 6,419,686 B1 | 7/2002 | McLeod et al. | |
| 6,423,052 B1 | 7/2002 | Escano | |
| 6,423,086 B1 | 7/2002 | Barbut et al. | |
| 6,425,909 B1 | 7/2002 | Dieck et al. | |
| 6,428,557 B1 | 8/2002 | Hilaire | |
| 6,428,558 B1 | 8/2002 | Jones et al. | |
| 6,428,559 B1 | 8/2002 | Johnson | |
| 6,432,122 B1 | 8/2002 | Gilson et al. | |
| 6,436,112 B2 | 8/2002 | Wensel et al. | |
| 6,436,120 B1 | 8/2002 | Meglin | |
| 6,436,121 B1 | 8/2002 | Blom | |

(56) References Cited

U.S. PATENT DOCUMENTS

| | | |
|---|---|---|
| 6,443,926 B1 | 9/2002 | Kletschka |
| 6,443,971 B1 | 9/2002 | Boylan et al. |
| 6,443,972 B1 | 9/2002 | Bosma et al. |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,454,775 B1 | 9/2002 | Demarais et al. |
| 6,458,139 B1 | 10/2002 | Palmer et al. |
| 6,458,145 B1 | 10/2002 | Ravenscroft et al. |
| 6,461,370 B1 | 10/2002 | Gray et al. |
| 6,468,290 B1 | 10/2002 | Weldon et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,500 B1 | 11/2002 | Kokish et al. |
| 6,485,501 B1 | 11/2002 | Green |
| 6,485,502 B2 | 11/2002 | Don Michael et al. |
| 6,491,712 B1 | 12/2002 | O'Connor |
| 6,494,895 B2 | 12/2002 | Addis |
| 6,497,709 B1 | 12/2002 | Heath |
| 6,499,487 B1 | 12/2002 | McKenzie et al. |
| 6,500,166 B1 | 12/2002 | Zadno Azizi et al. |
| 6,500,191 B2 | 12/2002 | Addis |
| 6,502,606 B2 | 1/2003 | Klint |
| 6,506,203 B1 | 1/2003 | Boyle et al. |
| 6,506,205 B2 | 1/2003 | Goldberg et al. |
| 6,508,826 B2 | 1/2003 | Murphy et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,559 B1 * | 2/2003 | O'Connell .................... 606/158 |
| 6,520,978 B1 | 2/2003 | Blackledge et al. |
| 6,520,983 B1 | 2/2003 | Colgan et al. |
| 6,527,746 B1 | 3/2003 | Oslund et al. |
| 6,527,791 B2 | 3/2003 | Fisher |
| 6,527,962 B1 | 3/2003 | Nadal |
| 6,530,935 B2 | 3/2003 | Wensel et al. |
| 6,530,939 B1 | 3/2003 | Hopkins et al. |
| 6,530,940 B2 | 3/2003 | Fisher |
| 6,533,770 B1 | 3/2003 | Lepulu et al. |
| 6,533,800 B1 | 3/2003 | Barbut |
| 6,537,293 B1 | 3/2003 | Berryman et al. |
| 6,537,294 B1 | 3/2003 | Boyle et al. |
| 6,537,296 B2 | 3/2003 | Levinson et al. |
| 6,537,297 B2 | 3/2003 | Tsugita et al. |
| 6,540,722 B1 * | 4/2003 | Boyle et al. .................. 604/106 |
| 6,540,767 B1 | 4/2003 | Walak et al. |
| 6,540,768 B1 | 4/2003 | Diaz et al. |
| 6,544,221 B1 | 4/2003 | Kokish et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,303 B1 | 4/2003 | Van Tassel et al. |
| 6,551,341 B2 | 4/2003 | Boylan et al. |
| 6,551,342 B1 | 4/2003 | Shen et al. |
| 6,554,849 B1 | 4/2003 | Jones et al. |
| 6,558,404 B2 | 5/2003 | Tsukernik |
| 6,558,405 B1 | 5/2003 | McInnes |
| 6,558,406 B2 | 5/2003 | Okada |
| 6,562,058 B2 | 5/2003 | Seguin et al. |
| 6,565,591 B2 | 5/2003 | Brady et al. |
| 6,569,147 B1 | 5/2003 | Evans et al. |
| 6,569,183 B1 | 5/2003 | Kim et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,579,303 B2 | 6/2003 | Amplatz |
| 6,582,396 B1 | 6/2003 | Parodi |
| 6,582,447 B1 | 6/2003 | Patel et al. |
| 6,582,448 B1 | 6/2003 | Boyle et al. |
| 6,589,227 B2 | 7/2003 | Klint |
| 6,589,230 B2 | 7/2003 | Gia et al. |
| 6,589,263 B1 | 7/2003 | Hopkins et al. |
| 6,589,264 B1 | 7/2003 | Barbut et al. |
| 6,589,265 B1 | 7/2003 | Palmer et al. |
| 6,589,266 B2 | 7/2003 | Whitcher et al. |
| 6,592,546 B1 | 7/2003 | Barbut et al. |
| 6,592,606 B2 | 7/2003 | Huter et al. |
| 6,592,616 B1 | 7/2003 | Stack et al. |
| 6,595,983 B2 | 7/2003 | Voda |
| 6,596,011 B2 | 7/2003 | Johnson et al. |
| 6,599,275 B1 | 7/2003 | Fischer, Jr. |
| 6,599,307 B1 | 7/2003 | Huter et al. |
| 6,599,308 B2 | 7/2003 | Amplatz |
| 6,602,271 B2 | 8/2003 | Adams et al. |
| 6,602,273 B2 | 8/2003 | Marshall |
| 6,602,280 B2 | 8/2003 | Chobotov |
| 6,605,102 B1 | 8/2003 | Mazzocchi et al. |
| 6,607,506 B2 | 8/2003 | Kletschka |
| 6,610,077 B1 | 8/2003 | Hancock et al. |
| 6,611,720 B2 | 8/2003 | Hata et al. |
| 6,613,074 B1 | 9/2003 | Mitelberg et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,623,506 B2 | 9/2003 | McGuckin, Jr. et al. |
| 6,629,953 B1 | 10/2003 | Boyd |
| 6,635,068 B1 | 10/2003 | Dubrul et al. |
| 6,635,069 B1 | 10/2003 | Teoh et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,638,372 B1 | 10/2003 | Abrams et al. |
| 6,641,590 B1 | 11/2003 | Palmer et al. |
| 6,641,605 B1 | 11/2003 | Stergiopulos |
| 6,645,160 B1 | 11/2003 | Heesch |
| 6,645,220 B1 | 11/2003 | Huter et al. |
| 6,645,221 B1 | 11/2003 | Richter |
| 6,645,222 B1 | 11/2003 | Parodi et al. |
| 6,645,223 B2 | 11/2003 | Boyle et al. |
| 6,645,224 B2 | 11/2003 | Gilson et al. |
| 6,652,554 B1 | 11/2003 | Wholey et al. |
| 6,652,557 B1 | 11/2003 | MacDonald |
| 6,652,558 B2 | 11/2003 | Patel et al. |
| 6,656,201 B2 | 12/2003 | Ferrera et al. |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,613 B1 | 12/2003 | Evans et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,676,682 B1 | 1/2004 | Tsugita et al. |
| 6,679,902 B1 | 1/2004 | Boyle et al. |
| 6,689,144 B2 | 2/2004 | Gerberding |
| 6,695,813 B1 | 2/2004 | Boyle et al. |
| 6,695,865 B2 | 2/2004 | Boyle et al. |
| 6,702,834 B1 | 3/2004 | Boylan et al. |
| 6,709,450 B2 | 3/2004 | Kang et al. |
| 6,712,835 B2 | 3/2004 | Mazzocchi et al. |
| 6,716,207 B2 | 4/2004 | Farnholtz |
| 6,716,231 B1 | 4/2004 | Rafiee et al. |
| 6,726,701 B2 | 4/2004 | Gilson et al. |
| 6,730,064 B2 | 5/2004 | Ragheb et al. |
| 6,755,855 B2 | 6/2004 | Yurek et al. |
| 6,755,856 B2 | 6/2004 | Fierens et al. |
| 6,758,855 B2 | 7/2004 | Fulton, III et al. |
| 6,761,727 B1 | 7/2004 | Ladd |
| 6,773,446 B1 | 8/2004 | Dwyer et al. |
| 6,773,448 B2 * | 8/2004 | Kusleika et al. .............. 606/200 |
| 6,774,278 B1 | 8/2004 | Ragheb et al. |
| 6,780,175 B1 | 8/2004 | Sachdeva et al. |
| 6,793,667 B2 | 9/2004 | Hebert et al. |

(56) References Cited

U.S. PATENT DOCUMENTS

| | | |
|---|---|---|
| 6,793,668 B1 | 9/2004 | Fisher |
| 6,833,002 B2 | 12/2004 | Stack et al. |
| 6,855,154 B2 | 2/2005 | Abdel-Gawwad |
| 6,866,677 B2 | 3/2005 | Douk et al. |
| 6,866,680 B2 | 3/2005 | Yassour et al. |
| 6,872,211 B2 | 3/2005 | White et al. |
| 6,878,153 B2 | 4/2005 | Linder et al. |
| 6,896,691 B2 | 5/2005 | Boylan et al. |
| 6,929,709 B2 | 8/2005 | Smith |
| 6,932,831 B2 | 8/2005 | Forber |
| 6,939,361 B1 | 9/2005 | Kieshinksi |
| 6,942,682 B2 | 9/2005 | Vrba et al. |
| 6,955,685 B2 | 10/2005 | Escamilla et al. |
| 6,964,670 B1 | 11/2005 | Shah et al. |
| 6,964,674 B1 | 11/2005 | Matsuura et al. |
| 6,969,396 B2 | 11/2005 | Krolik et al. |
| 6,974,469 B2 | 12/2005 | Broome et al. |
| 6,974,473 B2 | 12/2005 | Barclay et al. |
| 6,986,784 B1 | 1/2006 | Weiser et al. |
| 6,991,641 B2 | 1/2006 | Diaz et al. |
| 7,128,073 B1 | 10/2006 | Van Der Burg et al. |
| 7,166,120 B2 | 1/2007 | Kusleika |
| 7,174,636 B2 | 2/2007 | Lowe |
| 7,189,249 B2 | 3/2007 | Hart et al. |
| 7,255,687 B2 | 8/2007 | Huang et al. |
| 7,285,130 B2 | 10/2007 | Austin |
| 7,306,619 B1 | 12/2007 | Palmer |
| 7,371,248 B2 | 5/2008 | Dapolito et al. |
| 7,393,358 B2 | 7/2008 | Malewicz |
| 7,604,649 B2 | 10/2009 | McGuckin et al. |
| 7,666,216 B2 | 2/2010 | Hogendijk et al. |
| 7,731,722 B2 | 6/2010 | Lavelle et al. |
| 7,766,934 B2 * | 8/2010 | Pal et al. ............ 606/200 |
| 2001/0000799 A1 | 5/2001 | Wessman et al. |
| 2001/0001817 A1 | 5/2001 | Humes |
| 2001/0005789 A1 | 6/2001 | Root et al. |
| 2001/0007947 A1 | 7/2001 | Kanesaka |
| 2001/0011181 A1 | 8/2001 | DiMatteo |
| 2001/0011182 A1 | 8/2001 | Dubrul et al. |
| 2001/0012951 A1 | 8/2001 | Bates et al. |
| 2001/0016755 A1 | 8/2001 | Addis |
| 2001/0020175 A1 | 9/2001 | Yassour et al. |
| 2001/0023358 A1 | 9/2001 | Tsukernik |
| 2001/0025187 A1 | 9/2001 | Okada |
| 2001/0031980 A1 | 10/2001 | Wensel et al. |
| 2001/0031981 A1 | 10/2001 | Evans et al. |
| 2001/0031982 A1 | 10/2001 | Peterson et al. |
| 2001/0039431 A1 | 11/2001 | DeVries et al. |
| 2001/0039432 A1 | 11/2001 | Whitcher et al. |
| 2001/0041908 A1 | 11/2001 | Levinson et al. |
| 2001/0041909 A1 | 11/2001 | Tsugita et al. |
| 2001/0041928 A1 | 11/2001 | Pavcnik et al. |
| 2001/0044632 A1 | 11/2001 | Daniel et al. |
| 2001/0044634 A1 | 11/2001 | Don Michael et al. |
| 2001/0053921 A1 | 12/2001 | Jang |
| 2002/0002383 A1 | 1/2002 | Sepetka et al. |
| 2002/0002384 A1 | 1/2002 | Gilson et al. |
| 2002/0004667 A1 | 1/2002 | Adams et al. |
| 2002/0016564 A1 | 2/2002 | Courtney et al. |
| 2002/0016609 A1 | 2/2002 | Wensel et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0026212 A1 | 2/2002 | Wholey et al. |
| 2002/0026213 A1 | 2/2002 | Gilson et al. |
| 2002/0032460 A1 | 3/2002 | Kusleika et al. |
| 2002/0032461 A1 | 3/2002 | Marshall |
| 2002/0042626 A1 | 4/2002 | Hanson et al. |
| 2002/0042627 A1 | 4/2002 | Brady et al. |
| 2002/0045915 A1 | 4/2002 | Balceta et al. |
| 2002/0045916 A1 | 4/2002 | Gray et al. |
| 2002/0045918 A1 | 4/2002 | Suon et al. |
| 2002/0049452 A1 | 4/2002 | Kurz et al. |
| 2002/0049468 A1 | 4/2002 | Streeter et al. |
| 2002/0052627 A1 | 5/2002 | Boylan et al. |
| 2002/0058904 A1 | 5/2002 | Boock et al. |
| 2002/0058911 A1 | 5/2002 | Gilson et al. |
| 2002/0058963 A1 | 5/2002 | Vale et al. |
| 2002/0058964 A1 | 5/2002 | Addis |
| 2002/0062133 A1 | 5/2002 | Gilson et al. |
| 2002/0062134 A1 | 5/2002 | Barbut et al. |
| 2002/0062135 A1 | 5/2002 | Mazzocchi et al. |
| 2002/0065507 A1 | 5/2002 | Zadno-Azizi |
| 2002/0068954 A1 | 6/2002 | Foster |
| 2002/0068955 A1 | 6/2002 | Khosravi |
| 2002/0072764 A1 | 6/2002 | Sepetka et al. |
| 2002/0072765 A1 | 6/2002 | Mazzocchi et al. |
| 2002/0077596 A1 | 6/2002 | McKenzie et al. |
| 2002/0082558 A1 | 6/2002 | Samson et al. |
| 2002/0082639 A1 | 6/2002 | Broome et al. |
| 2002/0087187 A1 | 7/2002 | Mazzocchi et al. |
| 2002/0090389 A1 | 7/2002 | Humes et al. |
| 2002/0091407 A1 | 7/2002 | Zadno-Azizi et al. |
| 2002/0091408 A1 | 7/2002 | Sutton et al. |
| 2002/0091409 A1 | 7/2002 | Sutton et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099405 A1 | 7/2002 | Yurek et al. |
| 2002/0099407 A1 | 7/2002 | Becker et al. |
| 2002/0099435 A1 | 7/2002 | Stinson |
| 2002/0103501 A1 | 8/2002 | Diaz et al. |
| 2002/0107541 A1 | 8/2002 | Vale et al. |
| 2002/0111647 A1 | 8/2002 | Khairkhahan et al. |
| 2002/0111648 A1 | 8/2002 | Kusleika et al. |
| 2002/0111649 A1 | 8/2002 | Russo et al. |
| 2002/0116024 A1 | 8/2002 | Goldberg et al. |
| 2002/0120226 A1 | 8/2002 | Beck |
| 2002/0120286 A1 | 8/2002 | DoBrava et al. |
| 2002/0120287 A1 | 8/2002 | Huter |
| 2002/0123720 A1 | 9/2002 | Kusleika et al. |
| 2002/0123755 A1 | 9/2002 | Lowe et al. |
| 2002/0123759 A1 | 9/2002 | Amplatz |
| 2002/0123766 A1 | 9/2002 | Seguin et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133191 A1 | 9/2002 | Khosravi et al. |
| 2002/0133192 A1 | 9/2002 | Kusleika et al. |
| 2002/0138094 A1 | 9/2002 | Borillo et al. |
| 2002/0138095 A1 | 9/2002 | Mazzocchi et al. |
| 2002/0138096 A1 | 9/2002 | Hieshima |
| 2002/0138097 A1 | 9/2002 | Ostrovsky et al. |
| 2002/0143360 A1 | 10/2002 | Douk et al. |
| 2002/0143361 A1 | 10/2002 | Douk et al. |
| 2002/0143362 A1 | 10/2002 | Macoviak et al. |
| 2002/0151927 A1 | 10/2002 | Douk et al. |
| 2002/0151928 A1 | 10/2002 | Leslie et al. |
| 2002/0156520 A1 | 10/2002 | Boylan et al. |
| 2002/0161389 A1 | 10/2002 | Boyle et al. |
| 2002/0161390 A1 | 10/2002 | Mouw |
| 2002/0161391 A1 | 10/2002 | Murphy et al. |
| 2002/0161392 A1 | 10/2002 | Dubrul |
| 2002/0161393 A1 | 10/2002 | Demond et al. |
| 2002/0161394 A1 | 10/2002 | Macoviak et al. |
| 2002/0161395 A1 | 10/2002 | Douk et al. |
| 2002/0161396 A1 | 10/2002 | Jang et al. |
| 2002/0165557 A1 | 11/2002 | McAlister |
| 2002/0165573 A1 | 11/2002 | Barbut |
| 2002/0165576 A1 | 11/2002 | Boyle et al. |
| 2002/0165598 A1 | 11/2002 | Wahr et al. |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173819 A1 | 11/2002 | Leeflang et al. |
| 2002/0177872 A1 | 11/2002 | Papp et al. |
| 2002/0177899 A1 | 11/2002 | Eum et al. |
| 2002/0183781 A1 | 12/2002 | Casey et al. |
| 2002/0183782 A1 | 12/2002 | Tsugita et al. |
| 2002/0183783 A1 | 12/2002 | Shadduck |
| 2002/0188313 A1 | 12/2002 | Johnson et al. |
| 2002/0188314 A1 | 12/2002 | Anderson et al. |

(56) References Cited

U.S. PATENT DOCUMENTS

| | | |
|---|---|---|
| 2002/0193824 A1 | 12/2002 | Boylan et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1* | 12/2002 | Griffin et al. ............ 606/200 |
| 2002/0198561 A1 | 12/2002 | Amplatz |
| 2003/0004536 A1 | 1/2003 | Boylan et al. |
| 2003/0004537 A1 | 1/2003 | Boyle et al. |
| 2003/0004538 A1 | 1/2003 | Secrest et al. |
| 2003/0004539 A1 | 1/2003 | Linder et al. |
| 2003/0004540 A1 | 1/2003 | Linder et al. |
| 2003/0004541 A1 | 1/2003 | Wensel et al. |
| 2003/0004542 A1 | 1/2003 | Wensel et al. |
| 2003/0009146 A1 | 1/2003 | Muni et al. |
| 2003/0009189 A1 | 1/2003 | Gilson et al. |
| 2003/0009190 A1 | 1/2003 | Kletschka et al. |
| 2003/0009191 A1 | 1/2003 | Wensel et al. |
| 2003/0014072 A1 | 1/2003 | Wensel et al. |
| 2003/0018354 A1 | 1/2003 | Roth et al. |
| 2003/0018355 A1 | 1/2003 | Goto et al. |
| 2003/0023263 A1 | 1/2003 | Krolik et al. |
| 2003/0023264 A1 | 1/2003 | Dieck et al. |
| 2003/0023265 A1 | 1/2003 | Forber |
| 2003/0032976 A1 | 2/2003 | Boucck |
| 2003/0032977 A1 | 2/2003 | Brady |
| 2003/0040772 A1 | 2/2003 | Hyodoh et al. |
| 2003/0045897 A1 | 3/2003 | Huter et al. |
| 2003/0045898 A1 | 3/2003 | Harrison et al. |
| 2003/0050662 A1 | 3/2003 | Don Michael |
| 2003/0055452 A1 | 3/2003 | Joergensen et al. |
| 2003/0055480 A1 | 3/2003 | Fischell et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0065355 A1 | 4/2003 | Weber |
| 2003/0065356 A1 | 4/2003 | Tsugita et al. |
| 2003/0069596 A1 | 4/2003 | Eskuri |
| 2003/0073979 A1 | 4/2003 | Naimark et al. |
| 2003/0074019 A1 | 4/2003 | Gray et al. |
| 2003/0074054 A1 | 4/2003 | Duerig et al. |
| 2003/0078614 A1 | 4/2003 | Salahieh et al. |
| 2003/0083608 A1 | 5/2003 | Evans et al. |
| 2003/0083692 A1 | 5/2003 | Vrba et al. |
| 2003/0083693 A1 | 5/2003 | Daniel et al. |
| 2003/0088211 A1 | 5/2003 | Anderson et al. |
| 2003/0088266 A1 | 5/2003 | Bowlin |
| 2003/0093110 A1 | 5/2003 | Vale |
| 2003/0093112 A1 | 5/2003 | Addis |
| 2003/0097094 A1 | 5/2003 | Ouriel et al. |
| 2003/0097145 A1 | 5/2003 | Goldberg et al. |
| 2003/0100917 A1 | 5/2003 | Boyle et al. |
| 2003/0100918 A1 | 5/2003 | Duane |
| 2003/0100919 A1 | 5/2003 | Hopkins et al. |
| 2003/0105472 A1 | 6/2003 | McAlister |
| 2003/0105484 A1 | 6/2003 | Boyle et al. |
| 2003/0105486 A1 | 6/2003 | Murphy et al. |
| 2003/0109824 A1 | 6/2003 | Anderson et al. |
| 2003/0109897 A1 | 6/2003 | Walak et al. |
| 2003/0109916 A1 | 6/2003 | Don Michael |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0120304 A1 | 6/2003 | Kaganov et al. |
| 2003/0125764 A1 | 7/2003 | Brady et al. |
| 2003/0125765 A1 | 7/2003 | Blackledge et al. |
| 2003/0130680 A1* | 7/2003 | Russell ............ 606/200 |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135232 A1 | 7/2003 | Douk et al. |
| 2003/0135233 A1 | 7/2003 | Bates et al. |
| 2003/0139764 A1 | 7/2003 | Levinson et al. |
| 2003/0139765 A1 | 7/2003 | Patel et al. |
| 2003/0144685 A1 | 7/2003 | Boyle et al. |
| 2003/0144686 A1 | 7/2003 | Martinez et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0153944 A1 | 8/2003 | Phung et al. |
| 2003/0153945 A1 | 8/2003 | Patel et al. |
| 2003/0158518 A1 | 8/2003 | Schonholz et al. |
| 2003/0158574 A1 | 8/2003 | Esch et al. |
| 2003/0158575 A1 | 8/2003 | Boylan et al. |
| 2003/0163158 A1 | 8/2003 | White |
| 2003/0163159 A1 | 8/2003 | Patel et al. |
| 2003/0167068 A1 | 9/2003 | Amplatz |
| 2003/0167069 A1 | 9/2003 | Gonzales et al. |
| 2003/0171769 A1 | 9/2003 | Barbut |
| 2003/0171770 A1 | 9/2003 | Kusleika et al. |
| 2003/0171771 A1 | 9/2003 | Anderson et al. |
| 2003/0171772 A1 | 9/2003 | Amplatz |
| 2003/0171800 A1 | 9/2003 | Bicek et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176887 A1 | 9/2003 | Petersen |
| 2003/0176888 A1 | 9/2003 | O'Connell |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191492 A1 | 10/2003 | Gellman et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199917 A1 | 10/2003 | Knudson et al. |
| 2003/0199918 A1 | 10/2003 | Patel et al. |
| 2003/0199919 A1 | 10/2003 | Palmer et al. |
| 2003/0199920 A1 | 10/2003 | Boylan et al. |
| 2003/0199921 A1 | 10/2003 | Palmer et al. |
| 2003/0204168 A1 | 10/2003 | Bosma et al. |
| 2003/0204202 A1 | 10/2003 | Palmer et al. |
| 2003/0204203 A1 | 10/2003 | Khairkhahan et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0208253 A1 | 11/2003 | Beyer et al. |
| 2003/0212428 A1 | 11/2003 | Richter |
| 2003/0212429 A1 | 11/2003 | Keegan et al. |
| 2003/0212431 A1 | 11/2003 | Brady et al. |
| 2003/0212432 A1 | 11/2003 | Khairkhahan et al. |
| 2003/0212433 A1 | 11/2003 | Ambrisco et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0220667 A1 | 11/2003 | Van der Burg et al. |
| 2003/0225418 A1 | 12/2003 | Esksuri et al. |
| 2003/0225435 A1 | 12/2003 | Huter et al. |
| 2003/0229374 A1 | 12/2003 | Brady et al. |
| 2003/0233117 A1 | 12/2003 | Adams et al. |
| 2004/0006364 A1 | 1/2004 | Ladd |
| 2004/0006365 A1 | 1/2004 | Brady et al. |
| 2004/0006370 A1 | 1/2004 | Tsugita |
| 2004/0015152 A1 | 1/2004 | Day |
| 2004/0039412 A1 | 2/2004 | Isshiki et al. |
| 2004/0049226 A1 | 3/2004 | Keegan et al. |
| 2004/0054394 A1 | 3/2004 | Lee |

(56) References Cited

U.S. PATENT DOCUMENTS

| | | |
|---|---|---|
| 2004/0054395 A1 | 3/2004 | Lee et al. |
| 2004/0059372 A1 | 3/2004 | Tsugita |
| 2004/0064067 A1 | 4/2004 | Ward |
| 2004/0064179 A1 | 4/2004 | Linder et al. |
| 2004/0068271 A1 | 4/2004 | McAlister |
| 2004/0078044 A1 | 4/2004 | Kear |
| 2004/0082962 A1 | 4/2004 | Demarais et al. |
| 2004/0088038 A1 | 5/2004 | Dehnad et al. |
| 2004/0093009 A1 | 5/2004 | Denison et al. |
| 2004/0093012 A1 | 5/2004 | Cully et al. |
| 2004/0093016 A1 | 5/2004 | Root et al. |
| 2004/0093059 A1 | 5/2004 | Lee et al. |
| 2004/0098022 A1 | 5/2004 | Barone |
| 2004/0098026 A1 | 5/2004 | Joergensen et al. |
| 2004/0098033 A1 | 5/2004 | Leeflang et al. |
| 2004/0098112 A1 | 5/2004 | Dimatteo et al. |
| 2004/0102719 A1 | 5/2004 | Keith et al. |
| 2004/0106944 A1 | 6/2004 | Daniel et al. |
| 2004/0116831 A1 | 6/2004 | Vrba |
| 2004/0133232 A1 | 7/2004 | Rosenbluth et al. |
| 2004/0138696 A1 | 7/2004 | Drasler et al. |
| 2004/0153118 A1 | 8/2004 | Clubb et al. |
| 2004/0158278 A1 | 8/2004 | Becker et al. |
| 2004/0162576 A1 | 8/2004 | Barbut et al. |
| 2004/0164030 A1 | 8/2004 | Lowe et al. |
| 2004/0167567 A1 | 8/2004 | Cano et al. |
| 2004/0176794 A1 | 9/2004 | Khosravi |
| 2004/0176833 A1 | 9/2004 | Pavcnik et al. |
| 2004/0199203 A1 | 10/2004 | Oslund et al. |
| 2004/0204737 A1 | 10/2004 | Boismier et al. |
| 2004/0215322 A1 | 10/2004 | Kerr |
| 2004/0225321 A1 | 11/2004 | Krolik et al. |
| 2004/0236369 A1 | 11/2004 | Dubrul |
| 2005/0004663 A1 | 1/2005 | Llanos et al. |
| 2005/0021125 A1 | 1/2005 | Stack et al. |
| 2005/0027345 A1 | 2/2005 | Horan et al. |
| 2005/0038468 A1 | 2/2005 | Panetta et al. |
| 2005/0038503 A1 | 2/2005 | Greenhaigh |
| 2005/0043743 A1 | 2/2005 | Dennis |
| 2005/0043756 A1 | 2/2005 | Lavelle et al. |
| 2005/0043780 A1 | 2/2005 | Gifford et al. |
| 2005/0049668 A1 | 3/2005 | Jones et al. |
| 2005/0126979 A1 | 6/2005 | Lowe et al. |
| 2005/0137696 A1 | 6/2005 | Salahieh et al. |
| 2005/0149110 A1 | 7/2005 | Wholey et al. |
| 2005/0165480 A1 | 7/2005 | Jordan et al. |
| 2005/0177186 A1 | 8/2005 | Cully et al. |
| 2005/0177246 A1 | 8/2005 | Datta et al. |
| 2005/0197688 A1 | 9/2005 | Theron et al. |
| 2005/0209634 A1 | 9/2005 | Brady et al. |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009790 A1 | 1/2006 | Kleshinski et al. |
| 2006/0009798 A1 | 1/2006 | Callister et al. |
| 2006/0020334 A1 | 1/2006 | Lashinski et al. |
| 2006/0030923 A1 | 2/2006 | Gunderson |
| 2006/0074474 A1 | 4/2006 | Theron |
| 2006/0100544 A1 | 5/2006 | Ayala et al. |
| 2006/0100545 A1 | 5/2006 | Ayala et al. |
| 2006/0161241 A1 | 7/2006 | Barbut et al. |
| 2006/0184194 A1 | 8/2006 | Pal et al. |
| 2006/0200221 A1 | 9/2006 | Malewicz |
| 2006/0229660 A1 | 10/2006 | Pal et al. |
| 2006/0264707 A1 | 11/2006 | Kinney |
| 2006/0287668 A1 | 12/2006 | Fawzi et al. |
| 2007/0038241 A1 | 2/2007 | Pal |
| 2007/0100372 A1* | 5/2007 | Schaeffer ............... 606/200 |
| 2007/0112374 A1 | 5/2007 | Paul, Jr. et al. |
| 2007/0129752 A1* | 6/2007 | Webler et al. ............ 606/200 |
| 2007/0149996 A1 | 6/2007 | Coughlin |
| 2007/0167974 A1 | 7/2007 | Cully et al. |
| 2007/0185521 A1 | 8/2007 | Bui et al. |
| 2007/0250108 A1 | 10/2007 | Boyle et al. |
| 2007/0288054 A1 | 12/2007 | Tanaka et al. |
| 2008/0015518 A1 | 1/2008 | Huang et al. |
| 2008/0027481 A1 | 1/2008 | Gilson et al. |
| 2008/0103522 A1 | 5/2008 | Steingisser et al. |
| 2008/0154236 A1 | 6/2008 | Elkins et al. |
| 2008/0167629 A1 | 7/2008 | Dann et al. |
| 2008/0255587 A1 | 10/2008 | Cully et al. |
| 2008/0255606 A1 | 10/2008 | Mitra et al. |
| 2008/0262337 A1 | 10/2008 | Falwell et al. |
| 2008/0275569 A1 | 11/2008 | Lesh |

FOREIGN PATENT DOCUMENTS

| | | |
|---|---|---|
| EP | 1310219 A2 | 5/2003 |
| EP | 1516601 | 3/2005 |
| EP | 1557137 A1 | 7/2005 |
| WO | WO92/003097 | 3/1992 |
| WO | WO 96/010591 | 4/1996 |
| WO | WO 99/016382 | 4/1999 |
| WO | WO 99/023976 | 5/1999 |
| WO | WO 99/044510 | 9/1999 |
| WO | WO 01/082831 | 11/2001 |
| WO | WO 03/077799 A2 | 9/2003 |
| WO | WO 06/138391 A2 | 12/2006 |

OTHER PUBLICATIONS

Rubicon Embolic Filter, The Next Generation of EM, Rubicon Medical, www.rubiconmed.com.
Heeschen et al., Nature Medicine 7 (2001), No. 7, pp. 833-839.
Johnson et al., Circulation Research 94 (2004), No. 2, pp. 262-268.
International Search Report and Written Opinion for PCT/US2007/020300.
Brochure, "Shuttle Select™ System for Carotid Artery Access," (2004), pp. 1-3.
Brochure, "Slip-Cath® Angiographic Selective Catheters," (2004), pp. 1-6.
Finol, E.A. et al., "Performance Assessment of Embolic Protection Filters for Carotid Artery Stenting," *Modelling in Medicine and Biology IV*, (2005), vol. 8, pp. 133.
Grummon, David S. et al., Appl. Phys. Lett., 82,2727 (2003), pp. 2727.

* cited by examiner

EMBOLIC PROTECTION DEVICE INCLUDING A Z-STENT WAIST BAND

CROSS-REFERENCE TO RELATED APPLICATIONS

This application claims the benefit of U.S. Provisional Application Ser. No. 60/903,791, filed on Feb. 27, 2007, entitled "EMBOLIC PROTECTION DEVICE INCLUDING A Z-STENT WAIST BAND," the entire contents of which are incorporated herein by reference.

BACKGROUND OF THE INVENTION

1. Field of the Invention

The present invention generally relates to medical devices. More specifically, the invention relates to detachable and retrievable embolic protection devices for the capture of emboli during a vascular procedure.

2. Description of Related Art

Embolic protection devices are often used during and after medical procedures involving the vasculature to capture blood clots or other emboli before they enter the brain, causing a stroke, or enter the lungs, causing a pulmonary embolism. These devices are usually introduced by, for example, a catheterization procedure. They often need to be retrieved from the vasculature after an appropriate period of time using a similar catheterization procedure. Various protection devices exist but all have disadvantages. For example, some existing devices may not properly maintain the shape of a filter portion of the device, or the device may exert inadequate radial pressure against a body vessel wall.

In view of the above, it is apparent that there exists a need for an improved emboli protection device.

SUMMARY OF THE INVENTION

In satisfying the above need, as well as overcoming the enumerated drawbacks and other limitations of the related art, the present invention provides an embolic protection device for capturing emboli in a body vessel. The device includes a frame having an expanded state and a collapsed state. The frame has a plurality of struts extending distally along a longitudinal axis from a proximal end to a distal end. The struts are configured to open radially to define the expanded state of the device for capturing emboli and to fold along the longitudinal axis to define the collapsed state of the device for retrieval of the device. A waist band having an open and a closed state is attached to at least one of the plurality of struts of the frame. The waist band is formed of a plurality of members having proximal and distal tips. The proximal and distal tips of each member are alternatingly attached at a waist band joint to the respective proximal or distal tip of an adjacent member such that the members lie nearly parallel in the closed state and form a "Z" pattern in the open state. A filter portion is attached to the waist band and configured to capture emboli in the expanded state.

In some embodiments, a proximal stem extends longitudinally from the proximal end of the frame for deployment and retrieval of the device. The frame may also include at least two struts having proximal and distal sections that extend distally along the longitudinal axis. The proximal sections are connected together at the proximal end of the frame. The distal sections of the struts are connected together at the distal end of the frame such that the struts form an arc shaped portion. The distal arc shape portion may, for example, serve to provide shape and structure to the filter portion.

In another aspect of the present invention, the frame distally increases in width toward the waist band in the expanded state. In another example, each of the plurality of struts may be connected to at least one other strut at a frame joint. Each frame joint is configured to allow each of the struts to fold distally along the longitudinal axis from the expanded state to the collapsed state.

In another embodiment, the filter portion extends from the waist band to a distal filter end, the distal filter end is attached to the arc shape portion of the struts and configured to form a proximally facing concave shape.

In yet another embodiment, the filter portion is disposed about the waist band and further includes a proximal edge defining a filter opening when the device is in the expanded state for the capture of emboli.

In still other aspects of the present invention, the filter portion is a porous mesh cloth coated with a biocompatible polyurethane such as that marketed under the trade name THORALON. In some examples, the mesh cloth is made of nylon, polytetrafluoroethylene (PTFE), and mixtures thereof. In another example, the filter portion is a porous mesh cloth made of a biocompatible polyurethane such as THORALON.

In another example, at least part of the device is made of shape memory material configured to open the frame into the expanded state at a first temperature and close the frame into the collapsed state at a second temperature. The shape memory material includes alloys of Ni—Ti (Nitinol).

One embodiment of the present invention includes an assembly for placing and retrieving any of the devices described above in a body vessel. The assembly includes an outer sheath having a tubular body. The tubular body extends from a proximal part to a distal part and includes a lumen therethrough. The assembly also includes an inner member having proximal and distal portions. The inner member is disposed within the lumen of the outer sheath and configured for axial movement relative to the outer catheter. The embolic protection device is coaxially disposed within the lumen of the outer catheter and removably coupled to the distal portion of the inner catheter. The device is deployable through the distal part of the outer sheath by means of the relative axial movement of the inner member.

The present invention also includes a method of filtering emboli from a body cavity. The method includes providing an embolic protection device including a z-stent waist band and a THORALON filter portion within the body cavity. It also includes positioning the embolic protection device in a desired location to capture emboli within the filter portion, and expanding the embolic protection device within the body cavity.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 5B is an exploded view of the delivery and retrieval assembly of FIG. 5a;

DETAILED DESCRIPTION

Figure 1:
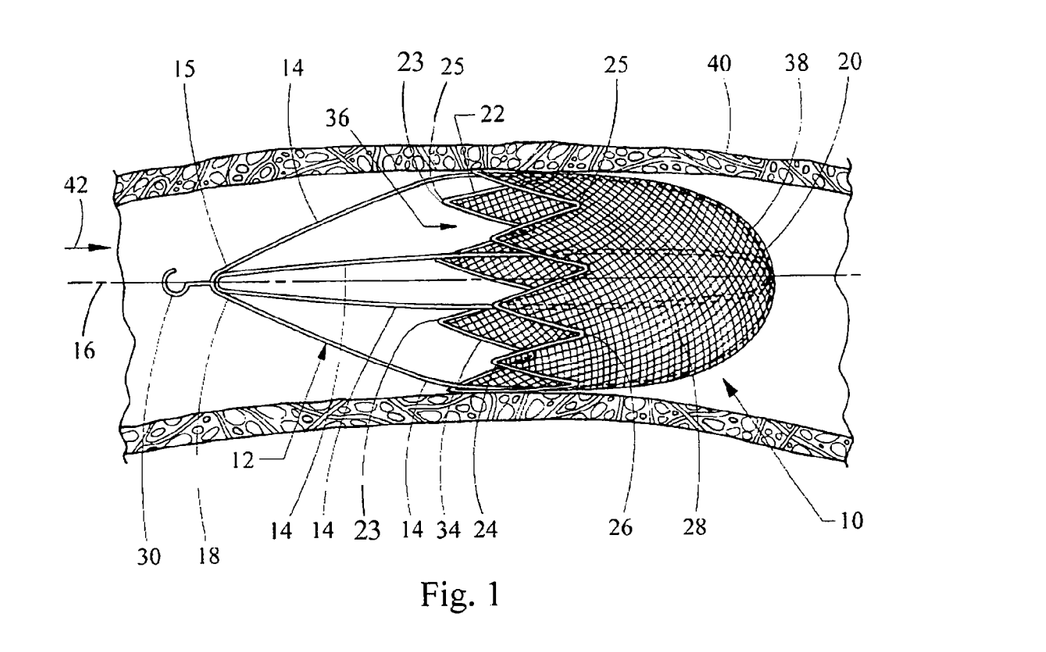
FIG. 1 is an environmental view of a retrievable filter device according to the present invention expanded in a body vessel.
Figure 2:
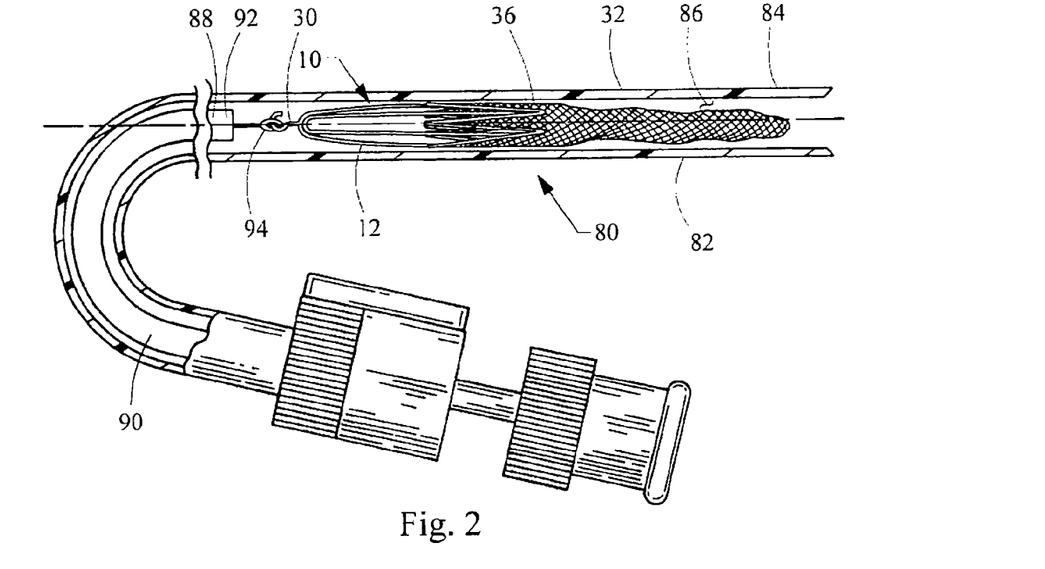
FIG. 2 is a side view of the filter device of FIG. 1 collapsed within one embodiment of a delivery and retrieval assembly.

Referring now to FIGS. 1 and 2, an embolic protection device embodying the principles of the present invention is illustrated therein and designated at 10. As its primary components, the device 10 includes a frame 12 having a plurality of struts 14 extending distally along a longitudinal axis 16 from a proximal end 18 to a distal end 20. A waist band 22 having an open and a closed state is disposed about the frame 12 between the proximal and distal ends 18 and 20. The waist band 22 is attached to at least one of the plurality of struts 14 and includes a filter portion 28. An optional proximal retrieval stem 30 extends from the proximal end 18 of the frame 12 for retrieval of the device 10.

The frame 12 has an expanded state for capturing emboli and a collapsed state for deployment and retrieval. As best shown in FIG. 1, the struts 14 are configured to open radially with respect to the longitudinal axis 16 to define the expanded state. As shown in FIG. 2, the struts 14 are also configured to fold along the longitudinal axis 16 to define the collapsed state for retrieval of the device 10 by, for example, a retrieval assembly 80. At least one strut 14 extends substantially along the longitudinal axis 16 and is joined to the waist band 22.

Returning to FIG. 1, the frame 12 distally increases in width toward the waist band 22 in the expanded state. Each of the plurality of struts 14 are connected to at least one other strut 14 at a frame joint 15. Each frame joint 15 is configured to allow each of the struts 14 to fold distally along the longitudinal axis 16 from the expanded state to the collapsed state. While the waist band 22 is shown disposed about the middle of the struts 14 of the frame 12, this is but one example of the present invention. In another example, the waist band 22 may be disposed within the struts 14. In still other examples the waist band 22 may be disposed elsewhere along the longitudinal axis 16 of the frame 12. For example, the waist band 22 may be disposed at the distal end 20 of the frame 12 such that each of the struts 14 end at the waist band 22 (not shown).

Figure 3:
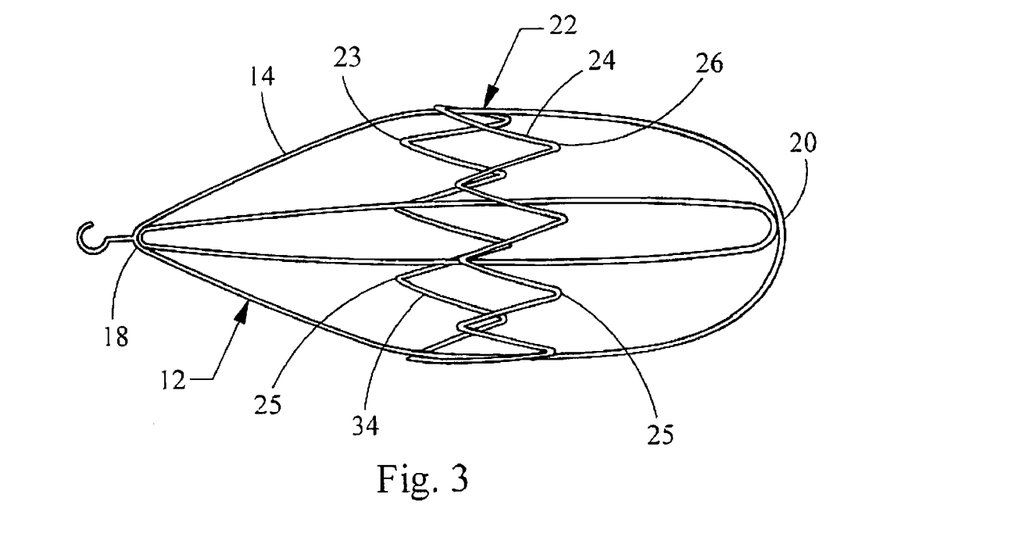
FIG. 3 is a perspective view of a retrievable filter device according to another embodiment of the present invention in an expanded state omitting a filter portion for clarity.
Figure 4:
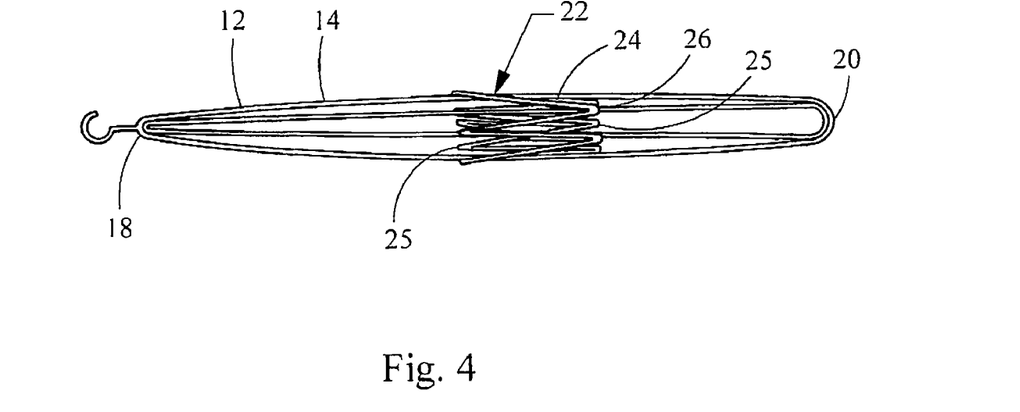
FIG. 4 is a perspective view of the retrievable filter device of FIG. 3 in a collapsed state.

Turning to FIG. 3, the waist band 22 has a ring shaped open state and a reduced diameter closed state. The waist band 22 is formed of a plurality of members 24 having proximal tips 20 and distal tips 26. The proximal and distal tips 20 and 26 of each member 24 are attached at a plurality of waist band joints 25 to the respective proximal and distal tips 20 and 26 of an adjacent member 24. As a result, the members 24 lie nearly parallel to each other in the closed state, as best shown in FIG. 4, and form a "Z" pattern in the open state, as best shown in FIG. 3. Adjacent struts 14 have at least one, at least two, or three waist band joints 25 disposed therebetween in the open state. It should be noted that FIGS. 3 and 4 omit the filter portion 28 to more clearly show the structure of the waist band 22.

At least part of the device 10 may be made of any suitable material such as a superelastic material, stainless steel wire, cobalt-chromium-nickel-molybdenum-iron alloy, or cobalt-chrome alloy. It is understood that the device 10 may be formed of any suitable material that will result in a self-opening or self-expanding device 10, such as shape memory material. Shape memory materials or alloys have the desirable property of becoming rigid, i.e., returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that material returns to its remembered state. The transition temperature is dependent on the relative proportions of the alloying elements Ni and Ti and the optional inclusion of alloying additives.

In one embodiment, the device 10 is made from Nitinol with a transition temperature that is slightly below normal body temperature of humans, which is about 98.6° F. Thus, when the device 10 is deployed in a body vessel and exposed to normal body temperature, the alloy of the device 10 will transform to austenite, that is, the remembered state, which for one embodiment of the present invention is the expanded state when the device 10 is deployed in the body vessel. To remove the device 10 it is cooled to transform the material to martensite which is more ductile than austenite, making the device 10 more malleable. As such, the device 10 can be more easily collapsed and pulled into a lumen of a catheter for removal.

In another embodiment, the device 10 is made from Nitinol with a transition temperature that is above normal body temperature of humans, which is about 98.6° F. Thus, when the device 10 is deployed in a body vessel and exposed to normal body temperature, the device 10 is in the martensitic state so that the device 10 is sufficiently ductile to bend or form into a desired shape, which for the present invention is the expanded state. To remove the device 10, the device 10 is heated to transform the alloy to austenite so that it becomes rigid and returns to a remembered state, which for the device 10 is a collapsed state.

The filter portion 28 extends from a proximal edge 34 to a distal filter end 38. The proximal edge 34 is joined to the waist band 22 and defines a filter opening 36. The proximal filter edge 34 (i.e. the proximal filter end) defines a "Z" pattern in the open state. The filter portion 28 is attached to the waist band 22 to allow emboli to enter the filter opening 36 and be captured within the filter portion 28. As shown at least in FIG. 1, the filter portion 28 is configured to form a proximally facing concave shape when in the expanded state. When introduced into a body vessel 40, the filter portion 28 may be oriented such that it faces into a direction of blood flow as indicated by the arrow 42.

The filter portion 28 includes a permeable mesh net or cloth made of any suitable material for capturing emboli while allowing blood and other fluids to flow past. In one embodiment, the mesh net or cloth may be made of nylon, biocompatible polyurethanes, polytetrafluoroethylene (known as PTFE or under the trade name Teflon™), and mixtures thereof without falling beyond the scope or spirit of the present invention. In one example, the permeable mesh cloth may be made of one material and coated with another, such as the biocompatible polyurethane. In another example, the mesh cloth may be made from the biocompatible polyurethane. In still another example, the filter portion 28 may be made of connective tissue material including, for example, extracellular matrix (ECM).

One example of the biocompatible polyurethane is sold under the trade name THORALON (THORATEC, Pleasanton, Calif.). Descriptions of suitable biocompatible polyureaurethanes are described in U.S. Pat. Application Publication No. 2002/0065552 A1 and U.S. Pat. No. 4,675,361, both of which are herein incorporated by reference. Briefly, these publications describe a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide either porous or non-porous structures. The present invention envisions the use of non-porous THORALON. Non-porous THORALON can be formed by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes/polycarbamates and urea linkages (hereinafter "—C(O)N or CON type polymers") may also be employed. These include CON type polymers that preferably include a soft segment and a hard segment. The segments can be combined as copolymers or as blends. For example, CON type polymers with soft segments such as PTMO, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

Preferably, the hard segment is formed from a diisocyanate and diamine. The diisocyanate may be represented by the formula OCN—R—NCO, where —R— may be aliphatic, aromatic, cycloaliphatic or a mixture of aliphatic and aromatic moieties. Examples of diisocyanates include MDI, tetramethylene diisocyanate, hexamethylene diisocyanate, trimethyhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3'-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible CON type polymers modified with cationic, anionic and aliphatic side chains may also be used. See, for example, U.S. Pat. No. 5,017,664. Other biocompatible CON type polymers include: segmented polyurethanes, such as BIOSPAN; polycarbonate urethanes, such as BIONATE; and polyetherurethanes, such as ELASTHANE; (all available from POLYMER TECHNOLOGY GROUP, Berkeley, Calif.).

Other biocompatible CON type polymers can include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane.

These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Application Publication No. 2002/0187288 A1, which is incorporated herein by reference.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

As noted above, the mesh cloth is made from, for example, a solid non-porous sheet of the biocompatible polyurethanes described above. After forming the sheet, a plurality of holes are formed in the sheet. The holes are sized to allow the free passage of blood and other bodily fluids while preventing the passage of emboli such as blood clots.

In other embodiments, the holes are formed at the same time the non-porous sheet is formed. For example, a mandrel formed from or coated with an inert material (e.g., glass or stainless steel) may be employed to facilitate manufacturing a biocompatible polyurethane mesh cloth. The mandrel may be cleaned with isopropyl alcohol prior to use and may then be immersed in a solution of the polyurethane, or alternatively, the mandrel may be sprayed with a solution of the polyurethane. The concentration of polyurethane in the solution may be fine tuned to provide the desired viscosity. The viscosity of the polyurethane solution may not only influence the rate of application, by dipping or spraying, but may also affect the thickness of the applied layer. The thickness of the layer may also be increased by dipping or spraying the mandrel repeatedly, until the desired thickness is achieved.

The mandrel may include a plurality of holes of an appropriate size and pattern for the mesh cloth. While the polyurethane is still liquid, a small vacuum or positive pressure may be applied through the holes to prevent the polyurethane from accumulating over the holes. When the polyurethane cures, it will have the shape of the mandrel and include the plurality of holes, matching the pattern of the holes on the mandrel.

As noted above, the filter portion 28 may also be made of connective tissue material for capturing emboli including, for example, extracellular matrix (ECM). As known, ECM is a complex structural entity surrounding and supporting cells found within tissues. More specifically, ECM includes structural proteins (for example, collagen and elastin), specialized protein (for example, fibrillin, fibronectin, and laminin), and proteoglycans, a protein core to which are attached long chains of repeating disaccharide units termed glycosaminoglycans.

In one particular embodiment, the extracellular matrix is comprised of small intestinal submucosa (SIS). As known, SIS is a resorbable, acellular, naturally occurring tissue matrix composed of ECM proteins and various growth factors. SIS is derived from the porcine jejunum and functions as a remodeling bioscaffold for tissue repair. SIS has characteristics of an ideal tissue engineered biomaterial and can act as a bioscaffold for remodeling of many body tissues including skin, body wall, musculoskeletal structure, urinary bladder, and also supports new blood vessel growth. In many aspects, SIS is used to induce site-specific remodeling of both organs and tissues depending on the site of implantation. In practice, host cells are stimulated to proliferate and differentiate into site-specific connective tissue structures, which have been shown to completely replace the SIS material in time.

In another particular embodiment, the SIS may be used to temporarily adhere the filter portion 28 to the walls of the body vessel 40 in which the device is deployed. SIS has a natural adherence or wetability to body fluids and connective cells comprising the connective tissue of a body vessel wall. Due to the temporary nature of the duration in which the device 10 is deployed in the body vessel, host cells of the wall may adhere to the filter portion but will not differentiate, allowing for later retrieval of the device 10 from the body vessel 40.

Returning to FIG. 2, the catheter assembly 80 for introducing and retrieving the embolic protection device 10 includes an outer sheath 82 having a distal part 84 and a tubular body defining a lumen 86 extending threrethrough. An inner member 88 having a proximal portion 90 extending to a distal portion 92 is disposed within the lumen 86 of the outer sheath 82 and is configured for axial movement relative to the outer sheath 82. The inner member 88 may be any appropriate type of elongate pushing device including, for example, an inner catheter, a stylet, or a wire guide. The device 10 is disposed within the lumen 86 of the outer sheath 82 with, for example, the proximal retrieval stem 30 being releasably attached to a complementary retrieval snare 94 of the distal portion 92 of the inner member 88. In another example, the proximal end 18 of the device 10 may be inseparably attached to the distal portion 92 of the inner member 88 (not shown). The device 10 is deployable through the distal part 84 of the outer sheath 82 by means of relative axial movement of the inner member 88. In the embodiment shown, the relative axial movement is either the inner member 88 being advanced distally through the lumen 86 relative to the outer sheath 82, or the outer sheath 82 is retracted proximally relative to the inner catheter 88.

Figure 5A:
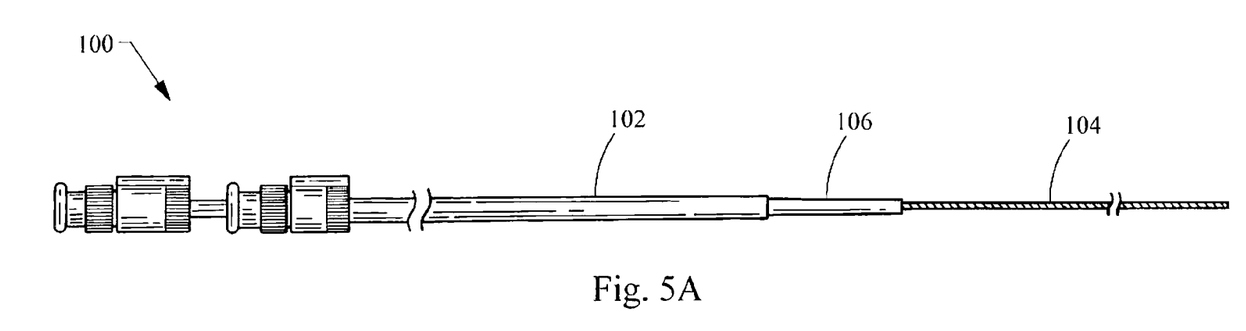
FIG. 5A is a side view of another embodiment of the delivery and retrieval assembly for use with the filter device of the present invention.
Figure 5B:
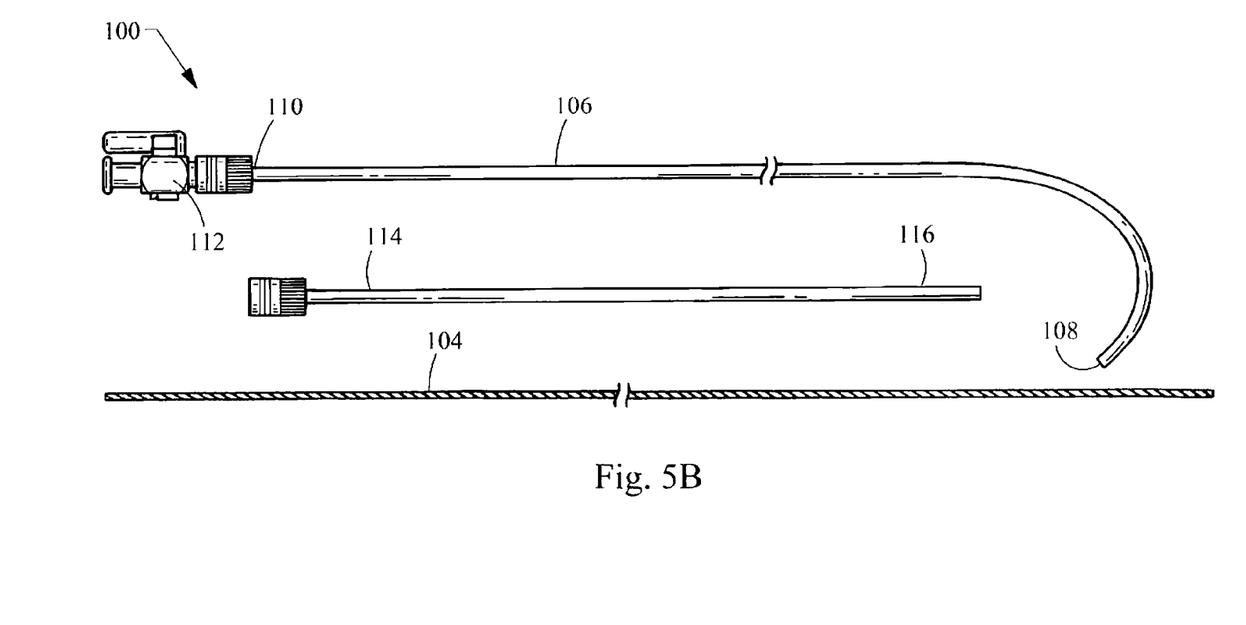

FIGS. 5A and 5B depict one embodiment of a delivery assembly 100 for introducing and retrieving the embolic protection device for capturing emboli in a body vessel in accordance with another embodiment of the present invention. As shown, the delivery assembly 100 includes a polytetrafluoroethylene (PTFE) introducer sheath 102 for percutaneously introducing an outer sheath 106 (equivalent to the outer catheter 82 above) into a body vessel. Of course, any other suitable material for the introducer sheath 102 may be used without falling beyond the scope or spirit of the present invention. The introducer sheath 102 may have any suitable size, for example, between about three-french to eight-french. The introducer sheath 102 serves to allow the outer sheath 106 and an inner member 114 to be percutaneously inserted to a desired location in the body vessel. The introducer sheath 102 receives the outer sheath 106 and provides stability to the outer sheath 106 at a desired location of the body vessel. The inner member 114 may be any appropriate elongate pushing device including, or example, a catheter, a stylet or a wire guide. For example, the introducer sheath 102 is held stationary within a common visceral artery, and adds stability to the outer sheath 106, as the outer sheath 106 is advanced through the introducer sheath 102 to a filtration area in the vasculature.

As shown, the assembly 100 may also include a wire guide 104 configured to be percutaneously inserted within the vasculature to guide the outer sheath 106 to the filtration area. The wire guide 104 provides the outer sheath 106 with a path to follow as it is advanced within the body vessel. The size of the wire guide 104 is based on the inside diameter of the outer sheath 106 and the diameter of the target body vessel.

In one example, when a distal end 108 of the outer sheath 106 is at the desired location in the body vessel, the wire guide 104 is removed and the filter device, having a proximal segment removably attached to a distal portion 116 of the inner member 114, is inserted into the outer sheath 106. The inner member 114 is advanced through the outer sheath 106 for deployment of the device through the distal end 108 to capture emboli in the body vessel during treatment of, for example, a lesion.

In another example, the wire guide 104 may be removed and a second wire guide inseparably attached to the filter device may be inserted and advanced through the outer sheath 106 for deployment of the device (not shown). In this example, the filter device remains attached to the second wire guide while, for example, an inner catheter is advanced along the second wire guide through the outer sheath 106 to treat the body vessel. As a result, the device may be removed immediately following treatment of the body vessel by simply withdrawing the second wire guide.

The outer sheath 106 further has a proximal end 110 and a hub 112 to receive the inner member 114 and device to be advanced therethrough. The size of the outer sheath 106 is based on the size of the body vessel in which it percutaneously inserts, and the size of the device.

In this embodiment, the device and inner member 114 are coaxially advanced through the outer sheath 106, following removal of the wire guide 104, in order to position the device to capture emboli in the body vessel. The device is guided through the outer sheath 106 by the inner member 114, preferably from the hub 112, and exits from the distal end 108 of the outer sheath 106 at a location within the vasculature where embolic protection is desired.

Likewise, this embodiment may also retrieve the device by positioning the distal end 108 of the outer sheath 106 adjacent the deployed device in the vasculature. The inner member 114 is advanced through the outer sheath 106 until the distal portion 116 protrudes from the distal end 108 of the outer sheath 106. The distal portion 116 is coupled to a proximal end of the device, after which the inner member 114 is retracted proximally, drawing the device into the outer sheath 106.

It is understood that the assembly described above is merely one example of an assembly that may be used to deploy the filter device in a body vessel. Of course, other apparatus, assemblies and systems may be used to deploy any embodiment of the embolic protection device without falling beyond the scope or spirit of the present invention.

Figure 6:
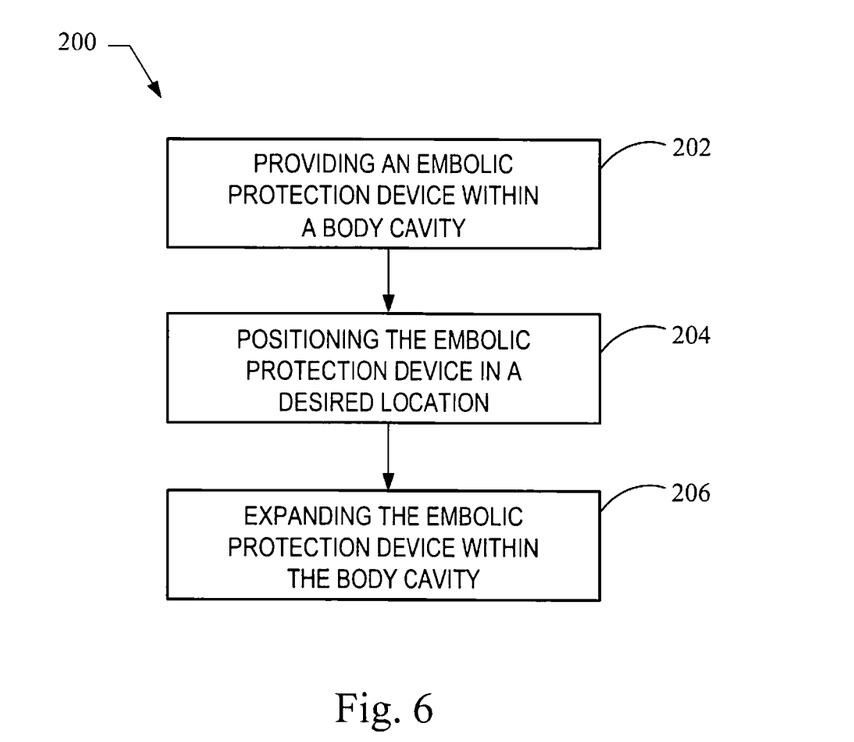
FIG. 6 is a flow-chart describing a method of filtering emboli using a device according to the present invention.

Turning to FIG. 6, it provides a flow chart designated at 200 describing a method for of filtering emboli from a body cavity such as a blood vessel. The method includes, at box 202, providing an embolic protection device including a Z-stent waist band and a filter portion within the body cavity. Box 204 includes positioning the embolic protection device in a desired location to capture emboli within the filter portion. Box 206 includes expanding the embolic protection device within the body cavity.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

I claim:

1. An embolic protection device for capturing emboli in a body vessel, the device comprising:
    a frame having an expanded state and a collapsed state, the frame including a plurality of struts extending distally along a longitudinal axis from a proximal end to a distal end, the struts being configured to open radially to define the expanded state of the device for capturing emboli and to fold along the longitudinal axis to define the collapsed state of the device for retrieval of the device;
    a waist band having an open and a closed state being disposed about the plurality of struts and attached to a middle portion of at least one of the plurality of struts of the frame, the waist band being formed of a plurality of members each having a proximal tip and a distal tip, each of the proximal and distal tips being attached at a waist band joint to the respective proximal or distal tip of an adjacent member such that the members form a "Z" pattern in the open state and lie nearly parallel to each other in the closed state, wherein adjacent struts have at least one waist band joint disposed therebetween in the open state; and
    a filter portion defining a proximal filter end attached to the waist band and a distal filter end attached to the distal end of the frame, the distal filter end defining a round shape when the frame is in the expanded state, the proximal filter end corresponding to the "Z" pattern of the waist band in the open state such that a portion of the proximal filter end is attached to the at least one waistband joint disposed between adjacent struts, the filter portion configured to capture emboli in the expanded state.

2. The device of claim 1, further comprising a proximal retrieval stem extending proximally from the proximal end of the frame for deployment and retrieval of the device.

3. The device of claim 1, wherein the frame includes at least two struts having proximal and distal sections and extending distally along the longitudinal axis, the proximal sections being connected together at the proximal end of the frame and the distal sections being connected together at the distal end of the frame such that the struts form a distal arc shape portion at the distal end of the frame.

4. The device of claim 3, wherein the filter portion extends from the waist band to a distal filter end, the distal filter end being attached to the distal arc shape portion to form a proximally facing concave shape.

5. The device of claim 3, wherein the proximal sections are connected together at a frame joint to define a proximal arc shape at the proximal end of the frame, the proximal arc shape forming a distally facing concave shape.

6. The device of claim 3, wherein the two struts each form a closed loop, and each of the closed loops are attached to diametrically opposed waistband joints.

7. The device of claim 1, wherein the frame distally increases in width toward the waist band in the expanded state.

8. The device of claim 1, wherein the waistband is disposed between the proximal and distal ends of the frame.

9. The device of claim 1, wherein each of the plurality of struts are connected to at least one other strut at a frame joint, each frame joint being configured to allow each of the struts to fold distally along the longitudinal axis from the expanded state to the collapsed state.

10. The device of claim 1, wherein the filter portion is a permeable mesh cloth including at least one of a biocompatible polyurethane, nylon, polytetrafluoroethylene, and mixtures thereof.

11. The device of claim 10, wherein the permeable mesh cloth is coated with biocompatible polyurethane.

12. The device of claim 1, wherein the filter portion is made of an extracellular matrix including small intestine submucosa.

13. The device of claim 1, wherein the filter portion is attached to the waist band and further includes a proximal edge defining a filter opening when the device is in the expanded state.

14. The device of claim 1, wherein at least part of the device is made of shape memory material configured to open the frame into the expanded state at a first temperature and close the frame into the collapsed state at a second temperature.

15. The device of claim 14, wherein the shape memory material includes alloys of Ni—Ti.

16. The device of claim 1, wherein adjacent struts have at least two waist band joints disposed therebetween in the open state.

17. An assembly for placing and retrieving an embolic protection device for capturing emboli in a body vessel, the assembly comprising:
an outer sheath having a tubular body, the tubular body including a lumen therethrough and having a distal part;
an inner member having a proximal and a distal portion, the inner member being disposed within the lumen of the outer sheath and configured for axial movement relative to the outer sheath;
an embolic protection device coaxially disposed within the lumen of the outer sheath and attached to the distal portion of the inner member, the device being deployable through the distal part of the outer sheath by means of the relative axial movement of the inner member, the device comprising:
a frame having an expanded state and a collapsed state, the frame including a plurality of struts extending distally along a longitudinal axis from a proximal end to a distal end, the struts being configured to open radially to define the expanded state of the device for capturing emboli and to fold along the longitudinal axis to define the collapsed state of the device for retrieval of the device;
a waist band having an open and a closed state being disposed about the plurality of struts and attached to the frame between the proximal and distal ends to a middle portion of at least one of the plurality of struts, the waist band being formed of a plurality of members each having a proximal tip and a distal tip, each of the proximal and distal tips being attached at a waist band joint to the respective proximal or distal tip of an adjacent member such that the members lie nearly parallel in the closed state and form a "Z" pattern in the open state, wherein adjacent struts have at least one waist band joint disposed therebetween in the open state; and
a filter portion defining a proximal filter end attached to the waist band and a distal filter end, the proximal filter end defining a "Z" pattern corresponding to the "Z" pattern of the waist band such that a portion of the proximal filter end is attached to the at least one waistband joint disposed between adjacent struts in the open state, the distal filter end defining a round shape when the frame is in the expanded state, the filter portion configured to capture emboli in the expanded state.

18. The assembly of claim 17, wherein the embolic protection device further includes a proximal retrieval stem extending proximally from the proximal end of the frame, the retrieval stem being removably attached to the inner member for deployment and retrieval of the device.

19. The assembly of claim 17, wherein the frame includes at least two struts having proximal and distal sections and extending distally along the longitudinal axis, the proximal sections being connected together at the proximal end of the frame and the distal sections being connected together such that the struts form a distal arc shape portion at the distal end of the frame.

20. The assembly of claim 19, wherein the filter portion extends from the waist band to a distal filter end, the distal filter end being attached to the distal arc shape portion to form a proximally facing concave shape.

21. The assembly of claim 17, wherein each of the struts are connected to at least one other strut at a frame joint, each frame joint being configured to allow the struts to fold distally along the longitudinal axis from the expanded state to the collapsed state.

22. The assembly of claim 17, wherein the filter portion is a permeable mesh cloth including a biocompatible polyurethane.

23. The assembly of claim 17, wherein at least part of the device is made of shape memory material including alloys of Ni—Ti.

24. An embolic protection device for capturing emboli in a body vessel, the device comprising:
a frame having an expanded state and a collapsed state, the frame including a plurality of struts extending distally along a longitudinal axis from a proximal end to a distal end, the struts being configured to open radially to define the expanded state of the device for capturing emboli and to fold along the longitudinal axis to define the collapsed state of the device for retrieval of the device;
a waist band having an open and a closed state being attached to a middle portion of at least one of the plurality of struts of the frame, the waist band being formed of a plurality of members each having a proximal tip and a distal tip, each of the proximal and distal tips being attached at a waist band joint to the respective proximal or distal tip of an adjacent member such that the members form a "Z" pattern in the open state and lie nearly parallel to each other in the closed state, wherein adjacent struts have at least one waist band joint disposed therebetween in the open state; and
a filter portion defining a proximal filter end attached to the waist band and a distal filter end attached to the distal end of the frame, the proximal filter end corresponding to the "Z" pattern of the waist band in the open state such that a portion of the proximal filter end is attached to the at least one waist band joint disposed between adjacent struts, the distal filter end defining a round shape when the frame is in the expanded state, the filter portion configured to capture emboli in the expanded state.

25. A method of filtering emboli from a body cavity having body walls, the method comprising:
providing an embolic protection device including a frame having a plurality of struts and having an expanded state and a collapsed state, a "Z" pattern waist band having an open and a closed state being disposed about the plurality of struts and attached to the frame between the proximal and distal ends to a middle portion of at least one of a plurality of struts, and a filter portion, the waist band being formed of a plurality of members each having a proximal tip and a distal tip, each of the proximal and distal tips being attached at a joint to a respective proximal or distal tip of an adjacent member such that the members form a "Z" pattern in the open state and lie nearly parallel in the closed state, the filter portion defining a proximal filter end attached to the waist band a distal filter end, the proximal filter end defining a "Z" pattern in the open state corresponding to the "Z" pattern of the waist band in the open state, wherein adjacent struts have at least one joint disposed therebetween in the open state, the distal filter end defining a round shape when the frame is in the expanded state and a portion of the proximal filter end is attached to the at least one joint disposed between adjacent struts;

positioning the embolic protection device in a desired location to capture emboli within the filter portion; and expanding the embolic protection device within the body cavity.

* * * * *